United States Patent
Nessim et al.

(10) Patent No.: US 11,690,601 B1
(45) Date of Patent: Jul. 4, 2023

(54) SYSTEM AND METHOD FOR PROCESSING MULTI-DIMENSIONAL ULTRASOUND IMAGING DATA ON REAL-TIME CLOUD COMPUTERS

(71) Applicant: Cloudstream Medical Imaging, Inc., Houston, TX (US)

(72) Inventors: Maurice Nessim, Houston, TX (US); Jun Tang, Houston, TX (US); Yi Luo, Houston, TX (US); Chuck Peng, Houston, TX (US)

(73) Assignee: Cloudstream Medical Imaging, Inc., Houston, TX (US)

( * ) Notice: Subject to any disclaimer, the term of this patent is extended or adjusted under 35 U.S.C. 154(b) by 0 days.

(21) Appl. No.: 17/943,806

(22) Filed: Sep. 13, 2022

Related U.S. Application Data (63) Continuation-in-part of application No. 17/712,919, filed on Apr. 4, 2022.

(51) Int. Cl.
*H04N 7/01* (2006.01)
*G01S 7/4865* (2020.01)
(Continued)

(52) U.S. Cl.
CPC ............ *A61B 8/5207* (2013.01); *A61B 8/463* (2013.01); *G01S 7/4865* (2013.01);
(Continued)

(58) Field of Classification Search
CPC . G06T 2207/10028; G06T 2207/30004; G06T 7/33; G06T 2207/10016;
(Continued)

(56) References Cited

U.S. PATENT DOCUMENTS 5,655,084 A * 8/1997 Pinsky ................... G16H 30/20
706/924
9,984,206 B2 5/2018 Spencer
(Continued)

FOREIGN PATENT DOCUMENTS

CN 109431606 A 3/2019
CN 111429460 B 9/2020
(Continued)

OTHER PUBLICATIONS

Fincke et al., Quantitative Sound Speed Imaging of Cortical Bone and Soft Tissue: Results From Observational Data Sets, Sep. 27, 2021 (1st public instance) [retrieved Nov. 23, 2022], IEEE Transactions on Medical Imaging, vol. 41, Issue: 3, pp. 502-514. (Year: 2021).*

(Continued)

*Primary Examiner* — Matthew C Bella
*Assistant Examiner* — Dennis Rosario
(74) *Attorney, Agent, or Firm* — Hunton Andrews Kurth LLP (57) ABSTRACT

The present embodiments relate generally to a system and method for generating images from ultrasound imaging data. The system can include a data acquisition processor, and administrator processor, a user device, and a server. The method can include transmitting images to a server, applying an implicit misfit function to generate a first set of images, then, based on this first set, apply an explicit misfit function to generate a second set of images of higher accuracy.

19 Claims, 5 Drawing Sheets

(51) Int. Cl.
*G06T 3/40* (2006.01)
*A61B 8/08* (2006.01)
*A61B 8/00* (2006.01)

(52) U.S. Cl.
CPC ......... *G06T 3/4092* (2013.01); *H04N 7/0117* (2013.01); *A61B 8/488* (2013.01)

(58) Field of Classification Search
CPC ............. G06T 7/30; G06T 2207/20221; G06T 7/0012; G06T 7/38; G06T 2207/10136; G06T 2207/10132; G06T 3/4007; G06T 3/40; G06T 3/4023; G06T 3/4053; G06T 3/4061; G06T 3/4069; G06T 3/4076; G06T 2207/30168; G06T 3/4092; G06T 2207/10088; G06T 2207/10072; G06T 2207/10116; G06T 7/207; G06T 2207/20208; G06T 2210/41; H04N 5/32; H04N 1/40068; H04N 21/2662; H04N 19/59; H04N 5/2628; H04N 23/667; H04N 21/234363; H04N 21/234381; H04N 21/440263; H04N 21/4728; H04N 25/42; H04N 13/194; H04N 21/440281; H04N 25/48; H04N 1/3871; H04N 23/815; H04N 23/951; H04N 7/0117; H04N 7/012; H04N 7/0122; H04N 1/33315; H04N 1/3935; H04N 1/393; H04N 21/25825; H04N 2201/325; H04N 2201/3251; H04N 21/4621; H04N 9/3188; H04N 19/50; H04N 21/440272; H04N 7/0125; H04N 7/0152; H04N 21/4356; H04N 23/632; H04N 13/139; H04N 23/69; H04N 19/53; H04N 2013/0088; H04N 2201/212; H04N 2201/0458; H04N 2201/3226; G01V 1/303; G01V 1/282; G01V 1/28; G01V 2210/6222; G01V 1/305; G08G 1/04; G01N 29/07; G01N 2291/011; G01N 29/024; G06V 10/754; H04L 27/183; H04L 27/3488; H04L 1/0041; H04L 67/12; H04L 1/0002; H04B 17/309; H04B 17/318; H04B 17/345; G01S 7/4865; G01S 17/894; G01S 3/50; G01S 7/003; G01S 7/52085; G01S 11/14; G01S 11/16; A61B 8/5207; A61B 8/52; A61B 2090/378; A61B 2034/2063; A61B 8/4477; A61B 8/469; A61B 8/46; A61B 8/461; A61B 8/462; A61B 8/463; A61B 8/464; A61B 8/465; A61B 8/466; A61B 8/467; A61B 8/468; A61B 8/00; A61B 8/4483; A61B 8/4494; A61B 6/5247; A61B 8/5215; A61B 8/4488; A61B 8/5261; A61B 8/5238; A61B 5/5246; A61B 8/5253
See application file for complete search history.

(56) References Cited

U.S. PATENT DOCUMENTS

| | | |
|---|---|---|
| 2012/0221728 A1 | 8/2012 | Dubbels et al. |
| 2013/0243282 A1 | 9/2013 | Sato et al. |
| 2015/0078126 A1 | 3/2015 | Lu |
| 2015/0110225 A1 | 4/2015 | Thevenin et al. |
| 2015/0369915 A1 | 12/2015 | Eibye et al. |
| 2015/0374347 A1 | 12/2015 | Manigoff et al. |
| 2016/0030000 A1* | 2/2016 | Sandhu ................. A61B 8/5207 600/448 |
| 2016/0220211 A1* | 8/2016 | Yamada ............... A61B 6/4266 |
| 2016/0232655 A1* | 8/2016 | Lachner .................. G06T 7/344 |
| 2020/0007516 A1* | 1/2020 | Westin ................ G06F 21/6254 |
| 2020/0253587 A1* | 8/2020 | Barannyk ............. A61B 8/485 |
| 2020/0351852 A1 | 11/2020 | McConnell et al. |
| 2021/0080573 A1 | 3/2021 | Bachmann et al. |
| 2021/0097641 A1 | 4/2021 | Iyer et al. |
| 2021/0166807 A1 | 6/2021 | Quennesson et al. |
| 2021/0215642 A1* | 7/2021 | Fincke ............... G01N 21/1702 |
| 2021/0308490 A1 | 10/2021 | Hu et al. |
| 2021/0339046 A1 | 11/2021 | Lachaine et al. |

FOREIGN PATENT DOCUMENTS

| | | | |
|---|---|---|---|
| DE | 4436263 A1 | 4/1996 | |
| DE | 102008037094 A1 | 11/2009 | |
| JP | 2010072765 A | 4/2010 | |
| WO | WO-2012154335 A2 * | 11/2012 | ........... A61B 5/0024 |

OTHER PUBLICATIONS

[item U continued] Retrieved: https://ieeexplore.ieee.org/abstract/document/9548889 (Year: 2021).*
Guasch et al., Full-waveform inversion imaging of the human brain, Mar. 6, 2020 [retrieved Nov. 23, 2022], npj Digital Medicine; vol. 3, Article No. 28 (2020), pp. 1-12. Retrieved: https://www.nature.com/articles/s41746-020-0240-8 (Year: 2020).*
Luo et al., Full-traveltime inversion, Jul. 18, 2016 (on-line) [retrieved Nov. 23, 2022], SEG Library: Geophysics, vol. 81, Iss: 5, pp. R261-R274. Retrieved: https://library.seg.org/doi/full/10.1190/geo2015-0353.1 (Year: 2016).*
Li et al., An improved automatic time-of-flight picker for medical ultrasound tomography, Jan. 2009 [retrieved Nov. 23, 2022], Ultrasonics, vol. 49, Issue: 1, pp. 61-72. Retrieved: https://www.sciencedirect.com/science/article/pii/S0041624X08000863 (Year: 2009).*
Non-final Office action dated Dec. 13, 2022 issued in U.S. Appl. No. 17/712,919, filed Apr. 4, 2022.

* cited by examiner

SYSTEM AND METHOD FOR PROCESSING MULTI-DIMENSIONAL ULTRASOUND IMAGING DATA ON REAL-TIME CLOUD COMPUTERS

FIELD OF DISCLOSURE

The present disclosure relates to systems and methods of processing multi-dimensional ultrasound imaging data by running a full travel time inversion method on cloud computers in real time.

BACKGROUND

The majority of current ultrasound imaging methods are essentially based on the delay and sum (DAS) principle. Once ultrasound signals are generated, they travel from the generating sources to scatters in tissues, bounce on the scatters, and continue traveling until recorded by receivers. The time spent on the entire traveling results in the delaying time, in regards to the emitting time of the recorded data. By removing the delaying time from the recorded data with a computation algorithm, one can place the reflecting singles over a trajectory of possible, but uncertain, scatter locations. If there are sufficient sources and receivers, these possible scatter trajectories will overlap on where the real scatters exist (i.e., true locations), and thus, many signals will sum up constructively and true locations will emerge in output images. Besides DAS, there are other imaging methods such as phase shift imaging, FK domain imaging and, finite reverse time imaging. All these imaging methods share same principle describe above that is true locations are common the all possible trajectories associated various source and receivers. However, the aforementioned methods share a common fault—there are no validation of the resulted images. The images, once generated, are used as final output without any verification and revisions.

To generate more accurate images, one can employ an inversion imaging method. Essentially, the inversion is a combination of two steps: imaging and modeling. In the modeling step, simulated input data are generated based on predetermined image and the sound velocity model. The simulated input data are compared to the recorded data. The difference between the two data sets, on the imaging step, are employed to revise the images and the sound velocity models used in the last modeling step. The two-step cycles are repeated until satisfactory images and velocity models are achieved or until a user's pre-defined maximum number of repetitions are reached. At the beginning of the modeling-imaging cycle, we must define an assumed initial velocity model (often set as uniform 1540 m/s of the water velocity) and image (often set to zeros). The most well-known method of inversion is the full waveform inversion (FWI) (Tarantola, A, 1987). Though FWI could produce sufficient images theoretically, it is susceptible to many out-of-control factors such as random noise, amplitudes flaws which are inevitable in practice, and many other unconsidered factors (e.g., elasticity and attenuation). Furthermore, FWI can produce wrong images and velocity models when the initial velocity model is not close to the true velocity distribution or when the observed ultrasound raw data lacks low frequency opponents.

The inversion methods have potential to make higher quality images compared to conventional imaging methods at the cost that more computation resources are necessary. The is obvious since the two-step cycle need repeat many times. Furthermore, sonographers need to see the measured results instantly. This conflict between high quality imaging results and real-time response requires more powerful and cost-effective computation resources. The cloud computer system can provide sufficient computation power on needed bases. The cloud system can eliminate the cost to buy a large computer system for every ultrasound system.

Due to the mentioned deficiencies of the imaging and the inversion methods, there is a need to provide a system and method that overcome these deficiencies. The system must provide real-time response in a cost-effective manner.

SUMMARY OF THE DISCLOSURE

Embodiments of the present disclosure provide a system for processing multi-dimensional, time-overlapping imaging data in real time using cloud computers. The system comprises a data acquisition processor, an administrator processor, a data storage unit, and a server. The data acquisition processor can receive one or more sets of multi-dimensional imaging data from one or more image collection devices. Additionally, the data acquisition processor can transmit the one or more sets of multi-dimensional imaging data over one or more express buses. The data storage unit is configured to store at least one or more sets of multi-dimensional imaging data. The administrator processor is coupled to the data storage unit. Furthermore, the administrator processor can receive the one or more sets of multi-dimensional imaging data from the data acquisition processor over one or more express buses. The server is configured to receive the one or more sets of multi-dimensional imaging data (i.e., ultrasound radio frequency data) over a network, and convert, by one or more processor further configured with a first predetermined function, the one or more sets of multi-dimensional imaging data into a first set of images (i.e., background sound velocity). Here, the first predetermined function is configured to implicitly convert the observed imaging data into the images without the use of pre-selected travel times. The end result of this first step is the background sound velocity distribution. Then the server can convert, by one or more processors further configured with a second predetermined function, the one or more sets of multi-dimensional imaging data and the resultant background velocity from the first step into a second set of images (scatter strength and sound velocity models). The second predetermined function is configured to explicitly convert the imaging data and the pre-selected travel times into images. The second step can be optionally approximated by subtraction of observed and simulated data; this leads to the least square imaging functions. Then determine, by a processor, whether the second of set of images has reached a predetermined resolution quality. Then, the processor converts the second set of imaging data into one or more displaying images. Then, the processor transmits, over the network, the one or more multi-dimensional displaying images to the administrator processor for reviewing by end users.

Embodiments of the present disclosure provide a method for processing multi-dimensional, time-overlapping imaging data in real time into images, the system comprising the following steps: receiving, by a data acquisition processor, one or more sets of multi-dimensional imaging data from one or more image collection devices; storing at least one or more sets of multi-dimensional imaging data in a data storage unit; transmitting, by the data acquisition processor, the one or more sets of multi-dimensional imaging data to a server; convert, by one or more processor further configured with a first predetermined function, the one or more sets of multi-dimensional imaging data into a first set of images; convert, by one or more processors further configured with a second predetermined function, the one or more sets of multi-dimensional imaging data into a second set of images; determine, by a processor, whether the second of set of imaging data has reached a predetermined resolution quality; convert, by the processor, the second set of imaging data into one or more displaying images; transmit, over the network, the one or more multi-dimensional displaying images to the administrator processor.

Embodiments of the present disclosure provide a computer readable non-transitory medium comprising computer executable instructions that, when executed on a processor, perform the following steps: receiving, by a data acquisition processor, one or more sets of multi-dimensional imaging data from one or more image collection devices; storing at least one or more sets of multi-dimensional imaging data in a data storage unit; transmitting, by the data acquisition processor, the one or more sets of multi-dimensional imaging data to a server; convert, by one or more processor further configured with a first predetermined function, the one or more sets of multi-dimensional imaging data into a first set of images; convert, by one or more processors further configured with a second predetermined function, the one or more sets of multi-dimensional imaging data into a second set of images; determine, by a processor, whether the second of set of images, via comparing the simulated imaging data generated by predetermined function on the sever with the observed imaging data, has reached a predetermined resolution quality; convert, by the processor, the second set of imaging data into one or more displaying images; transmit, over the network, the one or more multi-dimensional displaying images to the administrator processor.

BRIEF DESCRIPTION OF THE DRAWINGS

In order to facilitate a fuller understanding of the present invention, reference is now made to the attached drawings. The drawings should not be construed as limiting the present invention, but are intended only to illustrate different aspects and embodiments of the invention.

DETAILED DESCRIPTION

Exemplary embodiments of the invention will now be described in order to illustrate various features of the invention. The embodiments described herein are not intended to be limiting as to the scope of the invention, but rather are intended to provide examples of the components, use, and operation of the invention.

Furthermore, the described features, advantages, and characteristics of the embodiments may be combined in any suitable manner. One skilled in the relevant art will recognize that the embodiments may be practiced without one or more of the specific features or advantages of an embodiment. In other instances, additional features and advantages may be recognized in certain embodiments that may not be present in all embodiments.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The majority of current ultrasound imaging methods are based essentially on delay and sum (DAS) principle. This principle performs like this: ultrasound signals are generated, then the signals travel from their generating sources to scatter among the tissues of a patient, then they bounce off of the tissues, and finally they return back to the device from which they were generated. The DAS undoes the physical process. It removes the total time traveling from ultrasound generator to the scatter to the receiver, and sums the delay-time removed imaging data on every scanning scatter point. The summed outcome will show the scattering strengths on each imaging pixel. The strength of images on every grid (scanning) points or pixels indicate the scatter locations and difference from the background.

Besides DAS, inversion method can be used to generate better images using ultrasound methods. The inversion methods add a verification step to the DAS imaging function, and also repeat the imaging and verification steps until satisfactory results are achieved. Generally, there are two methods of inversion: the wave form and travel time inversion methods. For the waveform inversion, the representative and most well-known method is the full waveform inversion (FWI, Tarantola, A, 1987). In contrast, the full travel time inversion (FTI, Luo Y. et al., 2016) may be less known although it is more robust and practical than the FWI, as we will show in this invention. This is because that the waveform of ultrasound waves is vulnerable to many out-of-control factors, such as radon noise, inevitable unideal hardware response (e.g., coupling of transducer on skins), and uncounted physics (e.g., elastic and attenuation). The travel time may contain less information than the waveforms in theory—however, the information is much more reliable in practice. As a result, most FWI methods are modified to emphasize travel time (or phase) information, though they are remaining under the name of FWI. Rather than tweak the FWI to emphasize the travel time information, this invention constructs the inversion method directly utilizing the travel time information. A additional benefit of the FTI is that it is applicable to elastic inversion since the travel time concept remains the same regardless if the media is elastic or acoustic.

In general, any inversion method is computationally time consuming due to iterative computation of reconstructed model and methodically calculated data. On the other hand, it is critical to serve doctors in real time with images and sound speed estimation. In order to resolve the conflict of the real-time requirement and intense computational burden, we propose to implement the FTI on cloud computers in real time. To achieve the real time response, we must transfer raw data acquired on individual patient onto the cloud and the results to doctors for reviewing in real time, beside instant computation of the FTI itself. In other words, the full process needs to be in real time.

There are two ways to making use of travel time information—the explicit and implicit method to extract the travel time information. The explicit way is to pick, manually or automatically by computer algorithm, the travel time in advance, and serve the picked travel times as input for the FTI algorithm. The implicit way is to avoid the picking, and the travel time information will be implicitly utilized by the FTI algorithm via a misfit object function. In our inversion, we adopt both methods, in specific, we start the inversion using implicit method, followed by switching to the explicit method. The first step will guide the inversion to correct but low resolution solutions, and the second step will result in high resolution final outcome. The ability of our inversion to reconstruct correct and high-resolution solutions is illustrated with FIG. 1.

In inversion theory and algorithms, we usually need to compute the change of data (ultrasound waves) with respect to change of physical parameters (ultrasound speed). In order to perform pure travel time inversion, we should assume that the sound velocity change will cause only the change of travel time, no influence on amplitudes or waveforms. The assumption can ensure the consistent between the data (travel time) and the inversion mechanics. Most inversion algorithms have failed to honor this needed consistency; they are derived from a so-called Born approximation which cannot exclude amplitude changes from the fundamental theory. In our inversion, we have fixed this problem. In the rigorous mathematically languages, our FTI obeys the constrain that change of sound speed will only change of travel time, no influence on amplitude or waveforms.

Figure 1:
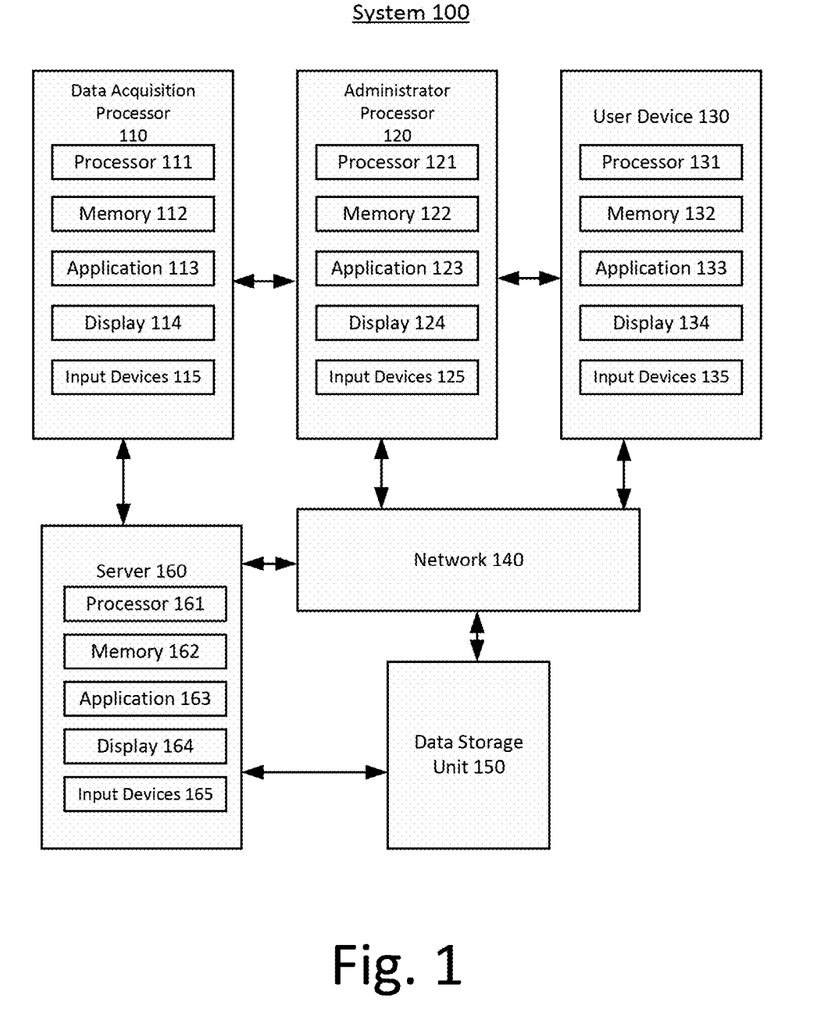
FIG. 1 is a block diagram illustrating a system according to an exemplary embodiment.

FIG. 1 is a block diagram illustrating a system according to an exemplary embodiment.

The system 100 can include a data acquisition processor 110, an administrator processor 120, a user device 130, a network 140, a data storage unit 150, and a server 160. Although FIG. 1 illustrates single instances of components of system 100, system 100 may include any number of components.

The system can include one or more data acquisition processors 110. The data acquisition processor 110 may include a processor 111, a memory 112, and an application 113. The processor 111 may be a processor, a microprocessor, or other processor, and the data acquisition processor 110 may include one or more of these processors. The processor 111 may include processing circuitry, which may contain additional components, including additional processors, memories, error and parity/CRC checkers, data encoders, anti-collision algorithms, controllers, command decoders, security primitives and tamper-proofing hardware, as necessary to perform the functions described herein.

The processor 111 may be coupled to the memory 112. The memory 112 may be a read-only memory, write-once read-multiple memory or read/write memory, e.g., RAM, ROM, and EEPROM, and the data acquisition processor 110 may include one or more of these memories. A read-only memory may be factory programmable as read-only or one-time programmable. One-time programmability provides the opportunity to write once then read many times. A write-once read-multiple memory may be programmed at one point in time. Once the memory is programmed, it may not be rewritten, but it may be read many times. A read/write memory may be programmed and re-programed many times after leaving the factory. It may also be read many times. The memory 112 may be configured to store one or more software applications, such as the application 113, and other data, such as user's private data and financial account information.

The application 113 may comprise one or more software applications, such as a mobile application and a web browser, comprising instructions for execution on the data acquisition processor 110. In some examples, the data acquisition processor 110 may execute one or more applications, such as software applications, that enable, for example, network communications with one or more components of the system 100, transmit and/or receive data, and perform the functions described herein. Upon execution by the processor 111, the application 113 may provide the functions described in this specification, specifically to execute and perform the steps and functions in the process flows described below. Such processes may be implemented in software, such as software modules, for execution by computers or other machines. The application 113 may provide graphical user interfaces (GUIs) through which a user may view and interact with other components and devices within the system 100. The GUIs may be formatted, for example, as web pages in HyperText Markup Language (HTML), Extensible Markup Language (XML) or in any other suitable form for presentation on a display device depending upon applications used by users to interact with the system 100.

The data acquisition processor 110 may further include a display 114 and input devices 115. The display 114 may be any type of device for presenting visual information such as a computer monitor, a flat panel display, and a mobile device screen, including liquid crystal displays, light-emitting diode displays, plasma panels, and cathode ray tube displays. The input devices 115 may include any device for entering information into the data acquisition processor 110 that is available and supported by the data acquisition processor 110, such as a touch-screen, keyboard, mouse, cursor-control device, touch-screen, microphone, digital camera, video recorder or camcorder. These devices may be used to enter information and interact with the software and other devices described herein.

The system can include one or more administrator processors 120. The administrator processors 120 may include a processor 121, a memory 122, and an application 123. The processor 121 may be a processor, a microprocessor, or other processor, and the administrator processors 120 may include one or more of these processors. The processor 121 may include processing circuitry, which may contain additional components, including additional processors, memories, error and parity/CRC checkers, data encoders, anti-collision algorithms, controllers, command decoders, security primitives and tamper-proofing hardware, as necessary to perform the functions described herein.

The processor 121 may be coupled to the memory 122. The memory 122 may be a read-only memory, write-once read-multiple memory or read/write memory, e.g., RAM, ROM, and EEPROM, and the administrator processors 120 may include one or more of these memories. A read-only memory may be factory programmable as read-only or one-time programmable. One-time programmability provides the opportunity to write once then read many times. A write-once read-multiple memory may be programmed at one point in time. Once the memory is programmed, it may not be rewritten, but it may be read many times. A read/write memory may be programmed and re-programed many times after leaving the factory. It may also be read many times. The memory 122 may be configured to store one or more software applications, such as the application 123, and other data, such as user's private data and financial account information.

The application 123 may comprise one or more software applications, such as a mobile application and a web browser, comprising instructions for execution on the administrator processor 120. In some examples, the administrator processor 120 may execute one or more applications, such as software applications, that enable, for example, network communications with one or more components of the system 100, transmit and/or receive data, and perform the functions described herein. Upon execution by the processor 121, the application 123 may provide the functions described in this specification, specifically to execute and perform the steps and functions in the process flows described below. Such processes may be implemented in software, such as software modules, for execution by computers or other machines. The application 123 may provide graphical user interfaces (GUIs) through which a user may view and interact with other components and devices within the system 100. The GUIs may be formatted, for example, as web pages in HyperText Markup Language (HTML), Extensible Markup Language (XML) or in any other suitable form for presentation on a display device depending upon applications used by users to interact with the system 100.

The administrator processor 120 may further include a display 124 and input devices 125. The display 124 may be any type of device for presenting visual information such as a computer monitor, a flat panel display, and a mobile device screen, including liquid crystal displays, light-emitting diode displays, plasma panels, and cathode ray tube displays. The input devices 125 may include any device for entering information into the administrator processor 120 that is available and supported by the administrator processor 120, such as a touch-screen, keyboard, mouse, cursor-control device, touch-screen, microphone, digital camera, video recorder or camcorder. These devices may be used to enter information and interact with the software and other devices described herein.

The system can include one or more user devices 130. The user device 130 may be a network-enabled computer device. Exemplary network-enabled computer devices include, without limitation, a server, a network appliance, a personal computer, a workstation, a phone, a handheld personal computer, a personal digital assistant, a thin client, a fat client, an Internet browser, a mobile device, a kiosk, or other a computer device or communications device. For example, network-enabled computer devices may include an iPhone, iPod, iPad from Apple® or any other mobile device running Apple's iOS® operating system, any device running Microsoft's Windows® Mobile operating system, any device running Google's Android® operating system, and/or any other smartphone, tablet, or like wearable mobile device.

The user device 130 may include a processor 131, a memory 132, and an application 133. The processor 131 may be a processor, a microprocessor, or other processor, and the user device 130 may include one or more of these processors. The processor 131 may include processing circuitry, which may contain additional components, including additional processors, memories, error and parity/CRC checkers, data encoders, anti-collision algorithms, controllers, command decoders, security primitives and tamper-proofing hardware, as necessary to perform the functions described herein.

The processor 131 may be coupled to the memory 132. The memory 132 may be a read-only memory, write-once read-multiple memory or read/write memory, e.g., RAM, ROM, and EEPROM, and the user device 130 may include one or more of these memories. A read-only memory may be factory programmable as read-only or one-time programmable. One-time programmability provides the opportunity to write once then read many times. A write-once read-multiple memory may be programmed at one point in time. Once the memory is programmed, it may not be rewritten, but it may be read many times. A read/write memory may be programmed and re-programed many times after leaving the factory. It may also be read many times. The memory 132 may be configured to store one or more software applications, such as the application 133, and other data, such as user's private data and financial account information.

The application 133 may comprise one or more software applications, such as a mobile application and a web browser, comprising instructions for execution on the user device 130. In some examples, the user device 130 may execute one or more applications, such as software applications, that enable, for example, network communications with one or more components of the system 100, transmit and/or receive data, and perform the functions described herein. Upon execution by the processor 131, the application 133 may provide the functions described in this specification, specifically to execute and perform the steps and functions in the process flows described below. Such processes may be implemented in software, such as software modules, for execution by computers or other machines. The application 133 may provide graphical user interfaces (GUIs) through which a user may view and interact with other components and devices within the system 100. The GUIs may be formatted, for example, as web pages in HyperText Markup Language (HTML), Extensible Markup Language (XML) or in any other suitable form for presentation on a display device depending upon applications used by users to interact with the system 100.

The user device 130 may further include a display 134 and input devices 135. The display 134 may be any type of device for presenting visual information such as a computer monitor, a flat panel display, and a mobile device screen, including liquid crystal displays, light-emitting diode displays, plasma panels, and cathode ray tube displays. The input devices 135 may include any device for entering information into the user device 130 that is available and supported by the user device 130, such as a touch-screen, keyboard, mouse, cursor-control device, touch-screen, microphone, digital camera, video recorder or camcorder. These devices may be used to enter information and interact with the software and other devices described herein.

System 100 may include one or more networks 140. In some examples, the network 140 may be one or more of a wireless network, a wired network or any combination of wireless network and wired network, and may be configured to connect the user device 130, the server 160, the data storage unit 150 and the server 160. For example, the network 140 may include one or more of a fiber optics network, a passive optical network, a cable network, an Internet network, a satellite network, a wireless local area network (LAN), a Global System for Mobile Communication, a Personal Communication Service, a Personal Area Network, Wireless Application Protocol, Multimedia Messaging Service, Enhanced Messaging Service, Short Message Service, Time Division Multiplexing based systems, Code Division Multiple Access based systems, D-AMPS, Wi-Fi, Fixed Wireless Data, IEEE 802.11b, 802.15.1, 802.11n and 802.11g, Bluetooth, NFC, Radio Frequency Identification (RFID), Wi-Fi, and/or the like.

In addition, the network 140 may include, without limitation, telephone lines, fiber optics, IEEE Ethernet 902.3, a wide area network, a wireless personal area network, a LAN, or a global network such as the Internet. In addition, the network 140 may support an Internet network, a wireless communication network, a cellular network, or the like, or any combination thereof. The network 140 may further include one network, or any number of the exemplary types of networks mentioned above, operating as a stand-alone network or in cooperation with each other. The network 140 may utilize one or more protocols of one or more network elements to which they are communicatively coupled. The network 140 may translate to or from other protocols to one or more protocols of network devices. Although the network 140 is depicted as a single network, it should be appreciated that according to one or more examples, the network 140 may comprise a plurality of interconnected networks, such as, for example, the Internet, a service provider's network, a cable television network, corporate networks, such as credit card association networks, and home networks. The network 140 may further comprise, or be configured to create, one or more front channels, which may be publicly accessible and through which communications may be observable, and one or more secured back channels, which may not be publicly accessible and through which communications may not be observable.

System 100 may include a database or data storage unit 150. The data storage unit 150 may be one or more databases configured to store data, including without limitation, private data of users, financial accounts of users, identities of users, transactions of users, and certified and uncertified documents. The database 150 may comprise a relational database, a non-relational database, or other database implementations, and any combination thereof, including a plurality of relational databases and non-relational databases. In some examples, the database 150 may comprise a desktop database, a mobile database, or an in-memory database. Further, the database 150 may be hosted internally by the server 130 or may be hosted externally of the server 160, such as by a server, by a cloud-based platform, or in any storage device that is in data communication with the server 160.

The system can include a server 160. The server 160 may be a network-enabled computer device. Exemplary network-enabled computer devices include, without limitation, a server, a network appliance, a personal computer, a workstation, a phone, a handheld personal computer, a personal digital assistant, a thin client, a fat client, an Internet browser, a mobile device, a kiosk, a contactless card, or other a computer device or communications device. For example, network-enabled computer devices may include an iPhone, iPod, iPad from Apple® or any other mobile device running Apple's iOS® operating system, any device running Microsoft's Windows® Mobile operating system, any device running Google's Android® operating system, and/or any other smartphone, tablet, or like wearable mobile device. The server may be a combination of one or more cloud computing systems such as public clouds, private clouds, and hybrid clouds.

The server 160 may include a processor 161, a memory 162, and an application 163. The processor 161 may be a processor, a microprocessor, or other processor, and the server 160 may include one or more of these processors. The processor 161 may include processing circuitry, which may contain additional components, including additional processors, memories, error and parity/CRC checkers, data encoders, anti-collision algorithms, controllers, command decoders, security primitives and tamper-proofing hardware, as necessary to perform the functions described herein.

The processor 161 may be coupled to the memory 162. The memory 162 may be a read-only memory, write-once read-multiple memory or read/write memory, e.g., RAM, ROM, and EEPROM, and the server 160 may include one or more of these memories. A read-only memory may be factory programmable as read-only or one-time programmable. One-time programmability provides the opportunity to write once then read many times. A write-once read-multiple memory may be programmed at one point in time. Once the memory is programmed, it may not be rewritten, but it may be read many times. A read/write memory may be programmed and re-programed many times after leaving the factory. It may also be read many times. The memory 162 may be configured to store one or more software applications, such as the application 163, and other data, such as user's private data and financial account information.

The application 163 may comprise one or more software applications, such as a mobile application and a web browser, comprising instructions for execution on the server 160. In some examples, the server 160 may execute one or more applications, such as software applications, that enable, for example, network communications with one or more components of the system 100, transmit and/or receive data, and perform the functions described herein. Upon execution by the processor 161, the application 163 may provide the functions described in this specification, specifically to execute and perform the steps and functions in the process flows described below. Such processes may be implemented in software, such as software modules, for execution by computers or other machines. The application 163 may provide graphical user interfaces (GUIs) through which a user may view and interact with other components and devices within the system 100. The GUIs may be formatted, for example, as web pages in HyperText Markup Language (HTML), Extensible Markup Language (XML) or in any other suitable form for presentation on a display device depending upon applications used by users to interact with the system 100.

The server 160 may further include a display 164 and input devices 165. The display 164 may be any type of device for presenting visual information such as a computer monitor, a flat panel display, and a mobile device screen, including liquid crystal displays, light-emitting diode displays, plasma panels, and cathode ray tube displays. The input devices 165 may include any device for entering information into the server 160 that is available and supported by the server 160, such as a touch-screen, keyboard, mouse, cursor-control device, touch-screen, microphone, digital camera, video recorder or camcorder. These devices may be used to enter information and interact with the software and other devices described herein.

Figure 2:
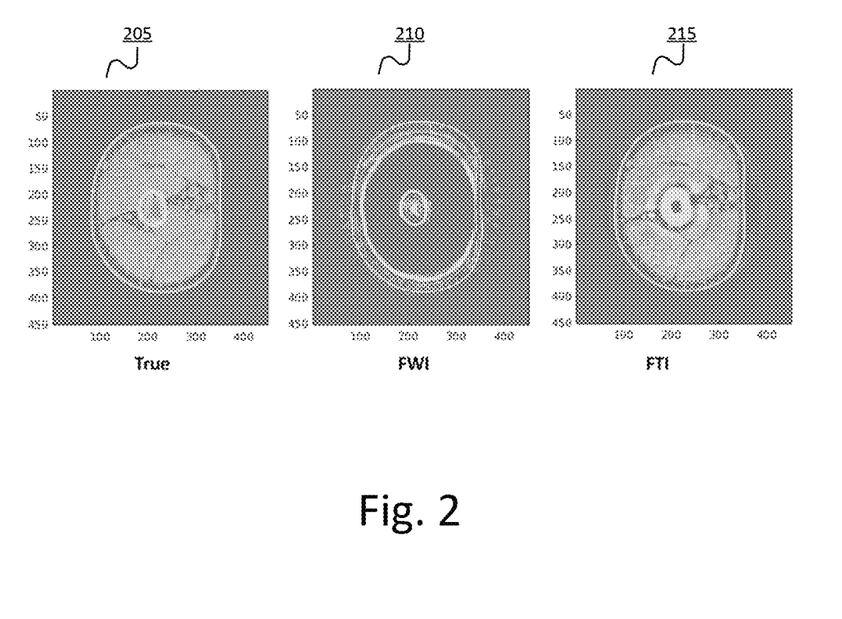
FIG. 2 is a diagram illustrating a method according to an exemplary embodiment.

FIG. 2 is a method diagram illustrating a process according to an exemplary embodiment.

The three images depict ultrasound renditions of a human arm. From left to right, the images are a true or most accurate rendition of a human arm 205, an FWI rendition of a human arm 210, and an FTI rendition of a human arm 215. These three images are presented to demonstrate the advantages of using the described FTI method as opposed to the more popular FWI method.

Both FWI and FTI rely on the foundational imaging technique known as inversion. Generally, inversion refers to the creation of multi-dimensional images based off of one or more data inputs, known constants, educated guesses, and other parameters. Several different techniques of inversion exist, but full waveform inversion (FWI) is the most commonly used inversion method for ultrasound imaging. As its name suggest, FWI uses waveform information as its primary method for generating images. Waveform information generally includes speed, amplitude, frequency, time, and other factors. Full time inversion (FTI), unlike FWI, does not base its calculations on waveform information. Rather, FTI relies only on travel time information to generate images. Thus, FTI relies on less information that FWI but avoids variables that interfere with image generations. For example, FTI does not rely on waveform amplitude which can interference significantly with image generation. In practice, FTI ultimately produces more accurate ultrasound images. The initial model used for both inversions are constant velocity 1540 m/s. Due to the presence of a human bone in the model 205 which is very different than the assumed water velocity, the FWI fails to reach right answer.

Figure 3:
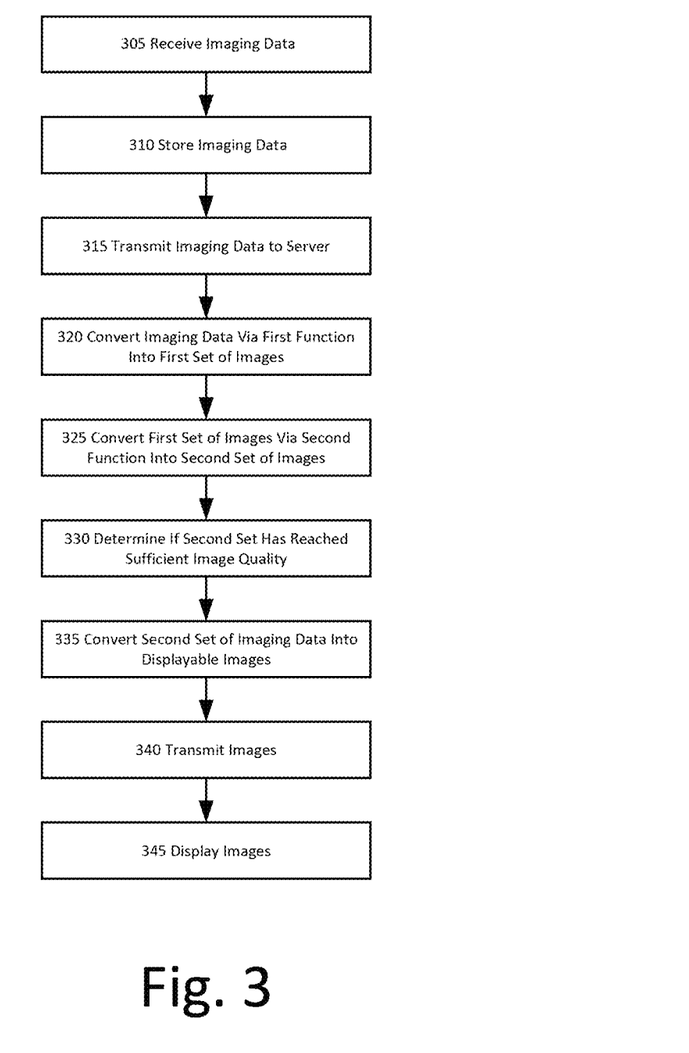
FIG. 3 is a flowchart illustrating a method according to an exemplary embodiment.

FIG. 3 is a method diagram illustrating a process according to an exemplary embodiment.

The method 300 can be performed between a data acquisition processor, an administrator processor, a network, a server, and a user device. These elements are discussed further with reference to FIG. 1.

In action 305, imaging data can be received. The data can include without limitation multi-dimensional imaging data such as time-shared transmissions, continuous recordings (CTCRs), and multiple beam transmit (MBT) recordings. The imaging data can be acquired by a data acquisition processor and transmitted to an administrator processor. The data acquisition processor can include device that can perform without limitation an abdominal ultrasound, bone sonometry, breast ultrasound, doppler fetal heart rate, doppler ultrasound, echocardiogram, fetal ultrasound, ultrasound-guided biopsies, ophthalmic ultrasound, or ultrasound-guided needle placement. The ultrasound procedure can be used without limitation to visualize abdominal tissues and organs, to asses bone fragility, to visualize breast tissue, to listen to a fetal heartbeat, to visualize blood flow through a blood vessel, organs, or other structures, to view the heart, to view the fetus in pregnancy, to collect a sample of tissue, to visualize ocular structures, or to assist in guiding needle placement in blood vessels or other tissues of interest. The data acquisition processor can include without limitation a stationary ultrasound device or portable ultrasound device. The administrator processor can include an intermediary device between the data acquisition processor and the server. As a nonlimiting example, the administrator processor can be associated with a user device or computer. As another nonlimiting example, the administrator processor can be couple with the data acquisition processor in one or more devices.

In action 310, the imaging data can be stored. As a nonlimiting example, the imaging data acquired by the data acquisition processor can be stored in a database or data storage unit. The database or data storage unit can be associated with the data acquisition processor, the administrator processor, the user device, the server, or some other predetermined data storage unit. The act of storing the data can be performed by a processor associated with either or both the data acquisition processor and the administrator processor. The data may be stored over a wireless or wired network such as an express bus within the data acquisition processor, administrator processor, user device, or server. In action 315, the imaging data is transmitted to the server. The data may be transmitted by either or both the data acquisition processor and the administrator processor. The imaging data can be transmitted offline to a server. As another nonlimiting example, the imaging data can be transmitted online to a cloud server. Cloud computing or cloud servers are discussed with further reference to FIG. 5.

In action 320, the server converts the imaging data into a first set of images via a first predetermined function. The conversion can be performed by a processor. The first set of images can include one or more stages of resolution. As a nonlimiting example, the first set of images can include images of varying quality but preferably in a manner of increasing quality. The first function can be an implicit misfit function. The implicit misfit function is discussed with further reference to FIG. 4. In action 325, the server converts the imaging data into a second set of images via a second predetermined function. The second set of images can include a higher quality resolution than the first set of images. The second function can be an explicit misfit function. The explicit misfit function is discussed with further reference to FIG. 4. In action 330, the server determines if the second set of images has reached a sufficient image quality. The determination can be carried out by a processor or some other predetermined function associated with the server. The sufficient image quality can be predetermined or dynamically determined by the user or some machine learning model.

In action 340, the images are transmitted. The images can be transmitted from the server to a user a device, the administrator processor, the data storage unit, or some other device. The images may be transmitted over a wireless or wired network. In action 345, the images can be displayed. The images can be displayed by the administrator processor, the user device, or some other device configured to display the images. The images can be displayed as standalone images or video. As a nonlimiting example, the images can be displayed on the user device as a video in real time. It is understood that the images can be transmitted continuously such that the images are displayed in real time. The ability to display the images in real time is due primarily to the server, which has a much higher computational speed and output than a traditional processor.

Figure 4:
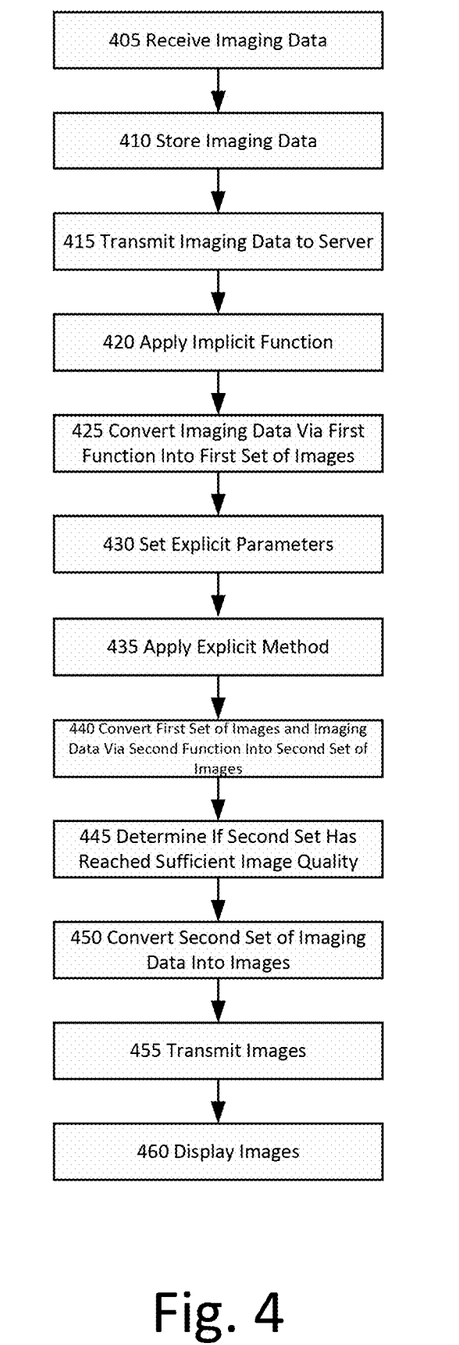
FIG. 4 is a flowchart illustrating a method according to an exemplary embodiment.

FIG. 4 is a method diagram illustrating a process according to an exemplary embodiment.

The method 400 can be performed between a data acquisition processor, an administrator processor, a network, a server, and a user device. These elements are discussed further with reference to FIG. 1.

In actions 405-415, imaging data can be received, stored, and transmitted to a server. The data can include without limitation multi-dimensional imaging data such as time-shared transmissions, continuous recordings (CTCRs), and multiple beam transmit (MBT) recordings. These actions are discussed with further reference to FIG. 3. The imaging data can be transmitted offline to a server. As another nonlimiting example, the imaging data can be transmitted online to a cloud server. Cloud computing or cloud servers are discussed with further reference to FIG. 5.

In action 420, the implicit function can be applied to the imaging data. The implicit function can be applied to a predetermined set of first images. The first set can be of varying size. The implicit function can be applied one-byone or in some other predetermined batching size. The implicit function can be described as a misfit function.

Generally there are two ways to making use of travel time information: the explicit and implicit method to extract the travel time information. The explicit way is to pick, manual or automatically by computer algorithm, the travel time in advance, and serve the picked travel times as input for the FTI algorithm. The implicit way is to avoid the picking, and the travel time information will be implicitly utilized by the FTI algorithm via a misfit object function. In our inversion, we adopt both methods, in specific, we start the inversion using implicit method, followed by switching to the explicit method. The first step will guide the inversion to correct but low resolution solutions, and the second step will result in high resolution final outcome.

A misfit function generally aims to minimize the error between an actual real-world model and a predicted model. The implicit misfit function is so-called because it does not rely on any explicit parameters. Rather, the implicit function records only what is generated in response to the ultrasound imaging results. Once the implicit function runs for a predetermined amount of time and a first set of images is generated. Both the implicit function and the explicit are FTI functions.

In this section, we derive the mathematical FTI formula. Starting from the constant velocity, we first perform the implicit FTI method to get a smooth background velocity developed into the first set of images. The misfit function we aim to minimize is defined as (de Hoop, et al., 2005; Luo, S., and P. Sava, 2011), $$\epsilon = \iint (\tau C)^2 dx_r dx_s \qquad (1)$$

C is the cross-correlation function between calculated data ($d_c$) and observed raw radio-frequency data ($d_o$) for the $x_r$ receiving channel and the source location $x_s$, $$C = \int d_o(t+\tau, x_r, x_s) d_c(t, x_g, x_s) dt \qquad (2)$$

Here, $\tau \in [-T, T]$ is a linear weight function that penalizes the correlation function C at non-zero time shifts.

It is assumed that the model slowness perturbation $\Delta s$ causes only travel time shift $\Delta \tau$ in the recorded wave signals. Therefore, ultrasound raw data is completely characterized by the travel times. For a single source-receiver pair, as the slowness model changes from s0 to s0+$\Delta s$, the channel data, $$d(t, x_r, x_s)_{s_0+\Delta s} = d(t+\Delta \tau, x_r, x_s)_{s_0} \qquad (3)$$

Accordingly, the derived correlation function C becomes, $$D(\tau, x_r, x_s)_{s_0+\Delta s} = C(\tau+\Delta \tau, x_r, x_s)_{s_0} \qquad (4)$$

Applying the conventional optimization method to Equation (1) and taking into account the constraint Equation 4, we can get the updated sound slowness from a previous slowness, $$s(x,z)_k = s(x,z)_{k-1} + \Delta s_k(x,z) \qquad (5)$$

Hehe, $$s = \frac{1}{v(x, z)},$$

v(x,z) is the sound speed on spatial location (x,z), k denotes the $k^{th}$ iteration, and k−1 indicate the previous known slowness distribution. The details update $\Delta s$ has been given by Y. Ma (2016). The initial model $s_0$ is often defined as a constant value everywhere. The most suitable constant for ultrasound image should be the water velocity 1540 meter per second. For making FIG. 1), we selected $s_0(x,z)$=1540.

Upon applying the implicit method in action 420, in action 425 the processor can arrive at a somewhat correct but low resolution imaging data described as the first set of images. In a nonlimiting example embodiment, it can be assume that the implicit method creates a somewhat correct rendition of the true model. This assumption is made because the implicit model is acting without any predetermined parameters. It is understood that the implicit method can arrive at different levels of resolution based on the context of each imaging project. Furthermore, it is understood that the implicit model can be performed for any length of time determined by the user or some machine learning model. The implicit model can be stopped and started at any time.

Having arrived a sufficient resolution, in actions 430 and 435 the explicit method can be applied. As its name suggests, the explicit method operates under an explicit set of parameters predetermined by the user or some machine learning model. As a nonlimiting example, if the goal is to generate an internal model of a human arm, the explicit method can integrate previous models of a human arm into its analysis. By starting the process with the implicit method and finishing with the explicit method, the process benefits by not being beholden to any previous models through the implicit model. The explicit model, although it relies on preexisting data, relies mainly on the findings of the implicit model. Furthermore, the explicit model can more quickly render the final images because the explicit model draws upon previous models.

The explicit FTI from the result of implicit FTI defined by Equation (1). The misfit function of explicit FTI is given by (Luo, Y., and G. T. Schuster, 1991), $$\epsilon = \iint (\Delta \tau)^2 dx_r dx_s \qquad (6)$$

Here, $\Delta \tau(x_r, x_s)$ is the picked travel time difference between observed and calculated channel radio frequency data. Applying the conventional derivation of the optimization problem Equation (6), the pseudo residual or used in the inversion is expressed by:

$$\delta r = \frac{d_c(t + \Delta t, x_r, x_s) - d_c(t, x_r, x_s)}{\Delta t} \Delta \tau \qquad (7)$$

When the known sound velocity is close to true velocity, the Equation (7) can be approximated by $$\delta r = \widetilde{d_o}(t, x_r, x_s) - d_c(t, x_r, x_s) \qquad (8)$$

Here, $\widetilde{d_o}$ is the observed data $d_o$ after scaled amplitude to match the amplitude of $d_c$. We assume the slightly shifted $d_c(t+\Delta t, x_r, x_s)$ is the same as the $d_o$, except the amplitudes need scaled to match each other. We also assumed that $\Delta t$ can be set as $\Delta \tau$, when $\Delta \tau$ is small (e.g., smaller than 1 forth of the time period at the dominant frequency). Equation (8) can generate high resolution inversion results as shown in FIG. 1.

When the initial velocity is smooth, there is no scattered waves, the $d_c(t, x_r, x_s)$=0. Keeping the fixed smoothed velocity as the background velocity, the full non-linear FTI becomes is reduced to a linear problem. The B-mode image is the solution to this linearized equation after first iteration, and the more iteration can generate higher quality images for the linearized problem. When the back ground velocity is not fixed, we need to perform the implicit FTI first to get the smooth velocity, followed by the linearized inversion to get the B-mode image or higher quality images with multiple iterations.

Upon applying the explicit method, in action 440 the processor can convert the first set of images into a second set of images. This action can be performed by a processor associated with the server. The approximate explicit function can be reduced to the least square migration or least square imaging when it is assumed that there is a linear relationship between the imaging data and sound set of images. Least square imaging is generally the subtraction of observed and simulated data. In action 445, the server can determine if the second set of images has reached a sufficient image quality. We then verify the second images can generate imaging data close to the observed imaging data. If the verification shows unsatisfied matching, we repeat the second explicitly step based on the mismatched residuals. This action can be performed by a processor or predetermined algorithm associated with the processor. The sufficiency of image quality can be predetermined or dynamically determined by a processor or algorithm. If the image quality is determined sufficient, then the second set of imaging data can be converted into one or more images in action 450. The imaging data can be converted into data one-by-one or in some batching fashion. This conversion can be performed by a processor associated with the server. Having converted the second set of imaging data into images, in action 455 the server can transmit the images. The images can be transmitted over a wireless or wired network such as an express bus. The server can transmit the images to a user device, an administrator processor, or some other device capable of receiving, storing, or displaying images. In action 460, the images can be displayed. The images can be displayed by a user device, administrator processor, or some other device. It is understood that the process is configured to display images in real time. The ability to display the images in real time is due primarily to the user of the server, which has a much higher computational speed and output than a traditional processor. Additionally, it is understood that although the images can be displayed in real time, the user can visually inspect the images by pausing, manipulating, zooming, or otherwise interacting with the images on the user device.

Figure 5:
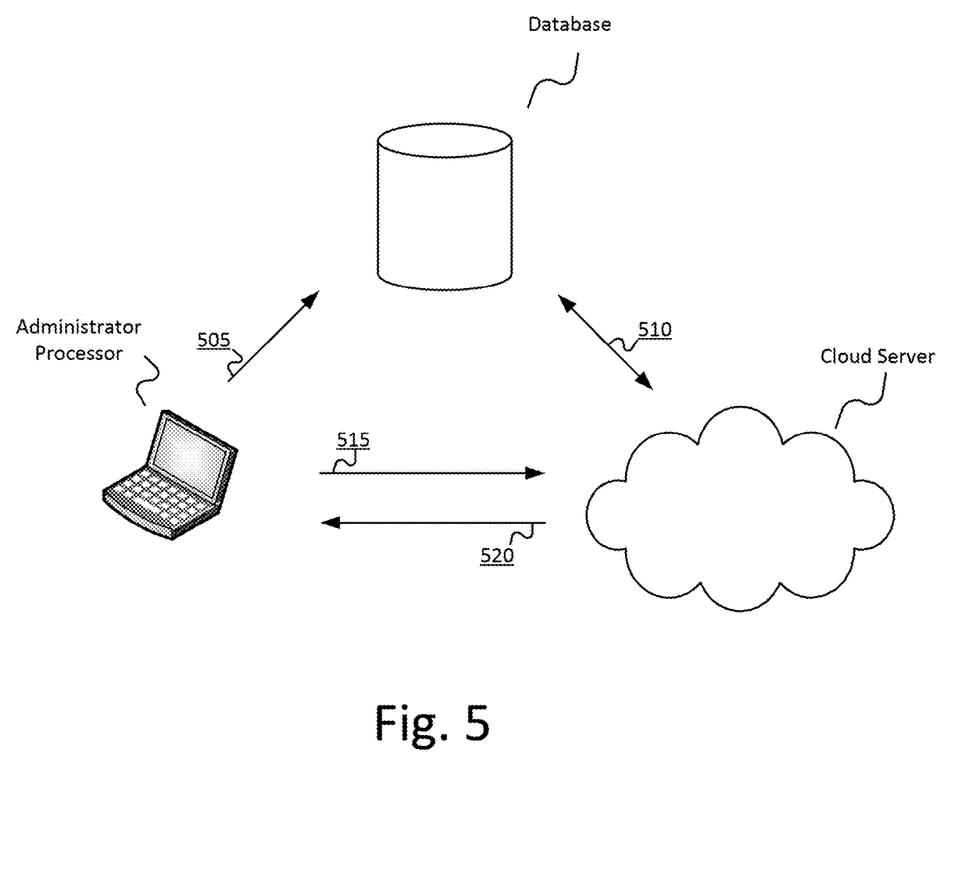
FIG. 5 is a diagram illustrating a method according to an exemplary embodiment.

FIG. 5 is a method diagram illustrating a process according to an exemplary embodiment.

The process 500 can include an administrator processor, a database, and a server. Each of the these elements are described further with reference to FIG. 1. In action 505, he administrator processor can transmit one or more sets of imaging data to the database. The data can include without limitation multi-dimensional imaging data such as time-shared transmissions, continuous recordings (CTCRs), and multiple beam transmit (MBT) recordings. Various kinds of information such as imaging data, images, and parameters can be selectively stored in the database. Similarly, in action 510 the server can transmit and receive one or more sets of imaging data from the database. In action 515, the administrator processor can transmit one or more sets of imaging data to the server where they can be processed. The server may be a combination of one or more cloud computing systems such as public clouds, private clouds, and hybrid clouds. The cloud server may be preconfigured with some predetermined algorithms to process the imaging data. The choice of imaging algorithms, parameters, and data processing workflows can be determined using a criterion matrix extracted from the geometry and dimension of the dataset. Each frame of ultrasound data can be processed on a single node or multiple nodes depends on the expected elapsed time and memory configuration. the server or cloud processor converts the imaging data into multi-dimensional images. This action can be performed by one or more processors associated with the server or cloud. This action can be performed frame-by-frame or in some batched manner. Additionally, the server or cloud may include one or more predetermined algorithms used to convert the data into multi-dimensional images. It is understood that although FIG. 5 describes a cloud server, other embodiments can include an offline transmission of imaging data to a server.

Having converted the imaging data, in action 520 the server or cloud processor transmits the multi-dimensional images over a network to the administrator processor. Alternatively, the multi-dimensional images can be sent to a user device. The images may be sent frame-by-frame or in some batched manner. Additionally, each frame can have an associated time stamp so that the administrator processor or user device can display the images or frames in a proper order even though the computation on the server or cloud might have placed them out of order. It is understood that the administrator processor displays the images in real time. Alternatively, the user device may display the images.

Although embodiments of the present invention have been described herein in the context of a particular implementation in a particular environment for a particular purpose, those skilled in the art will recognize that its usefulness is not limited thereto and that the embodiments of the present invention can be beneficially implemented in other related environments for similar purposes. The invention should therefore not be limited by the above described embodiments, method, and examples, but by all embodiments within the scope and spirit of the invention as claimed.

In the invention, various embodiments have been described with references to the accompanying drawings. It may, however, be evident that various modifications and changes may be made thereto, and additional embodiments may be implemented, without departing from the broader scope of the invention as set forth in the claims that follow. The invention and drawings are accordingly to be regarded in an illustrative rather than restrictive sense.

The invention is not to be limited in terms of the particular embodiments described herein, which are intended as illustrations of various aspects. Many modifications and variations can be made without departing from its spirit and scope. Functionally equivalent systems, processes and apparatuses within the scope of the invention, in addition to those enumerated herein, may be apparent from the representative descriptions herein. Such modifications and variations are intended to fall within the scope of the appended claims. The invention is to be limited only by the terms of the appended claims, along with the full scope of equivalents to which such representative claims are entitled.

It is further noted that the systems and methods described herein may be tangibly embodied in one or more physical media, such as, but not limited to, a compact disc (CD), a digital versatile disc (DVD), a floppy disk, a hard drive, read only memory (ROM), random access memory (RAM), as well as other physical media capable of data storage. For example, data storage may include random access memory (RAM) and read only memory (ROM), which may be configured to access and store data and information and computer program instructions. Data storage may also include storage media or other suitable type of memory (e.g., such as, for example, RAM, ROM, programmable read-only memory (PROM), erasable programmable read-only memory (EPROM), electrically erasable programmable read-only memory (EEPROM), magnetic disks, optical disks, floppy disks, hard disks, removable cartridges, flash drives, any type of tangible and non-transitory storage medium), where the files that comprise an operating system, application programs including, for example, web browser application, email application and/or other applications, and data files may be stored. The data storage of the network-enabled computer systems may include electronic information, files, and documents stored in various ways, including, for example, a flat file, indexed file, hierarchical database, relational database, such as a database created and maintained with software from, for example, Oracle® Corporation, Microsoft® Excel file, Microsoft® Access file, a solid state storage device, which may include a flash array, a hybrid array, or a server-side product, enterprise storage, which may include online or cloud storage, or any other storage mechanism. Moreover, the figures illustrate various components (e.g., servers, computers, processors, etc.) separately. The functions described as being performed at various components may be performed at other components, and the various components may be combined or separated. Other modifications also may be made.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, to perform aspects of the present invention.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions specified herein. These computer-readable program instructions may also be stored in a computer-readable storage medium that can direct a computer, a programmable data processing apparatus, and/or other devices to function in a manner, such that the computer readable storage medium having instructions stored therein comprises an article of manufacture including instructions which implement aspects of the functions specified herein.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions specified herein.

What is claimed is:

1. A system for processing multi-dimensional, time-overlapping imaging data in real time, the system comprising:
   a data acquisition processor configured to receive one or more sets of multi-dimensional imaging data from one or more image collection devices, the data acquisition processor further configured to transmit the one or more sets of multi-dimensional imaging data over one or more express buses;
   a data storage unit configured to store at least the one or more sets of multi-dimensional imaging data;
   an administrator processor coupled to the data storage unit, the administrator processor further configured to receive the one or more sets of multi-dimensional imaging data from the data acquisition processor over the one or more express buses; and
   a server configured to receive the one or more sets of multi-dimensional imaging data over a network, and convert by one or more processors configured with a first predetermined function the one or more sets of multi-dimensional imaging data into a first set of images, wherein the first predetermined function is further configured to convert the one or more sets of multi-dimensional imaging data without a use of preselected travel times, then convert by the one or more processors further configured with a second predetermined function the one or more sets of multi-dimensional imaging data and the first set of images into a second set of images, wherein the second predetermined function is further configured to explicitly convert the one or more sets of multi-dimensional imaging data with the use of pre-selected travel times, then determine by the one or more processors whether the second set of images has reached a predetermined resolution quality, then convert by the one or more processors the second set of images into one or more multi-dimensional displaying images, then transmit over the network the one or more multi-dimensional displaying images to the administrator processor.

2. The system of claim 1, wherein the data acquisition processor is further configured to receive one or more sets of multi-dimensional imaging data comprising at least time-shared transmissions, continuous recordings (CTCRs), and multiple beam transmit (MBT) recordings.

3. The system of claim 1, wherein the first predetermined function is an implicit wave-equation-based inversion function and is a cross-correlational function between a set of calculated data and observed raw radio-frequency data for a receiving channel and a source location.

4. The system of claim 1, wherein the second predetermined function is an explicit wave-equation-based inversion function further configured to minimize a picked travel time difference between an observed and a calculated set of channel radio frequency data.

5. The system of claim 1, wherein the first and second predetermined functions operate under the assumptions that (1) sound velocity change will cause only the change in travel time and no change in wave amplitude or waveform and (2) the ultrasound waves propagate in media obeys the acoustic wave equation, rather the approximated ray equation.

6. The system of claim 1, wherein the set of multi-dimensional imaging data further comprise ultrasound signals generated by bouncing ultrasound waves off of one or more internal human body parts.

7. The system of claim 1, wherein the server further comprises one or more cloud computing systems.

8. The system of claim 7, wherein the cloud computing systems comprises at least public cloud computing systems, private cloud computing systems, and hybrid cloud computing systems.

9. A method for processing multi-dimensional, time-overlapping imaging data in real time, the method comprising:
receiving by a data acquisition processor one or more sets of multi-dimensional imaging data from one or more image collection devices;
storing at least the one or more sets of multi-dimensional imaging data in a data storage unit;
transmitting by the data acquisition processor the one or more sets of multi-dimensional imaging data to a server;
convert by one or more processors further configured with a first predetermined function the one or more sets of multi-dimensional imaging data into a first set of multi-dimensional imaging data wherein the first set of multi-dimensional imaging data is of a first resolution quality;
convert by one or more processors further configured with a second predetermined function the first set of multi-dimensional imaging data into a second set of multi-dimensional imaging data wherein the second set of multi-dimensional imaging data is of a second resolution quality;
determine by the one or more processors whether the second of set of multi-dimensional imaging data has reached a predetermined resolution quality threshold;
convert by the one or more processors the second set of multi-dimensional imaging data into one or more multi-dimensional displaying images; and
transmit over a network the one or more multi-dimensional displaying images to an administrator processor;
wherein the first predetermined function is further configured to convert the one or more sets of multi-dimensional imaging data without a use of pre-selected travel times.

10. The method of claim 9, wherein the second predetermined function is further configured to explicitly convert the image data with a use of pre-selected travel times.

11. The method of claim 9, wherein the first and second predetermined functions operate under an assumption that sound velocity change will cause only the change in travel time and no change in wave amplitude or waveform, and the assumption that ultrasound wave propagation is determined by an acoustic wave equation, rather a broadly-adopted ray equation.

12. The method of claim 9, wherein the set of multi-dimensional imaging data further comprise ultrasound signals generated by bouncing ultrasound waves off of one or more human body parts.

13. The method of claim 9, wherein the data acquisition processor is further configured to receive one or more sets of multi-dimensional imaging data comprising at least time-shared transmissions, continuous recordings (CTCRs), and multiple beam transmit (MBT) recordings.

14. The method of claim 9, wherein upon determining that the second of set of imaging data has reached a predetermined resolution quality, the method comprises a step of converting the one or more sets of multi-dimensional imaging data into a second set of images.

15. A computer readable non-transitory medium comprising computer executable instructions that, when executed on a processor, perform procedures comprising the steps of:
receiving by a data acquisition processor one or more sets of multi-dimensional imaging data from one or more image collection devices;
storing at least the one or more sets of multi-dimensional imaging data in a data storage unit;
transmitting by the data acquisition processor the one or more sets of multi-dimensional imaging data to a server;
convert by one or more processors further configured with a first predetermined function, the one or more sets of multi-dimensional imaging data into a first set of images;
convert by the one or more processors further configured with a second predetermined function the one or more sets of multi-dimensional imaging data and the first set of images into a second set of images;
determine by the one or more processors whether the second of set of images has reached a predetermined resolution quality;
convert by the one or more processors the second set of images into one or more multi-dimensional displaying images; and
transmit over a network the one or more multi-dimensional displaying images to the administrator processor;
wherein the first predetermined function is further configured to convert the one or more sets of multi-dimensional imaging data without a use of pre-selected travel times.

16. The computer readable non-transitory medium of claim 15, wherein upon determining that the second of set of imaging data has reached a predetermined resolution quality, the method comprises the step of converting the one or more sets of multi-dimensional imaging data into a second set of images.

17. The computer readable non-transitory medium of claim 15, wherein upon transmitting the one or more multi-dimensional images to the administrator processor, the images are displayed on a user device associated with ultrasound imaging.

18. The computer readable non-transitory medium of claim 15, wherein the first predetermined function is $\in = \iint (\tau C)^2 dx_r dx_s$ wherein C is the cross-correlation function between calculated data ($d_c$) and observed raw radio-frequency data ($d_o$) for the $x_r$ receiving channel and the source location $x_s$.

19. The computer readable non-transitory medium of claim 15, wherein the second predetermined algorithm $\in = \iint (\Delta\tau) dx_r dx_s$ wherein $\Delta\tau(x_r, x_s)$ is the picked travel time difference between observed ($d_o$) and calculated channel radio frequency data ($d_r$) wherein $\Delta\tau$ is minimized according to an acoustic wave equation, rather than a broadly-adopted ray theory.

* * * * *